United States Patent [19]
Ayers

[11] Patent Number: 5,476,498
[45] Date of Patent: Dec. 19, 1995

[54] CORONARY SINUS CHANNEL LEAD AND METHOD

[75] Inventor: Gregory M. Ayers, Duvall, Wash.

[73] Assignee: InControl, Inc., Redmond, Wash.

[21] Appl. No.: 290,606

[22] Filed: Aug. 15, 1994

[51] Int. Cl.⁶ ............................................. A61N 1/05
[52] U.S. Cl. .................... 607/122; 607/126; 128/642
[58] Field of Search ..................... 607/119, 116, 607/122, 126; 128/642

[56] References Cited

U.S. PATENT DOCUMENTS

| | | | |
|---|---|---|---|
| 4,154,247 | 5/1979 | O'Neill | 128/419 |
| 4,414,986 | 11/1983 | Dickhudt et al. | 128/785 |
| 4,706,671 | 11/1987 | Weinrib | 128/348.1 |
| 4,825,871 | 5/1989 | Cansell | 128/419 |
| 4,852,573 | 8/1989 | Kennedy | 128/642 |
| 4,860,769 | 8/1989 | Fogarty et al. | 128/786 |
| 5,016,808 | 5/1991 | Heil, Jr. et al. | 228/176 |
| 5,170,802 | 12/1992 | Mehra | 127/784 |
| 5,221,261 | 6/1993 | Termin et al. | 604/104 |
| 5,235,977 | 8/1993 | Hirschberg et al. | 607/5 |
| 5,256,146 | 10/1993 | Ensminger et al. | 604/104 |
| 5,279,299 | 1/1994 | Imran | 128/642 |
| 5,387,233 | 2/1995 | Alferness et al. | 607/126 |

FOREIGN PATENT DOCUMENTS

| | | | |
|---|---|---|---|
| 0601338 | 6/1994 | European Pat. Off. | A61N 1/05 |
| 0601339 | 6/1994 | European Pat. Off. | A61N 1/05 |

*Primary Examiner*—William L. Kamm
*Assistant Examiner*—Kennedy J. Schaetzle
*Attorney, Agent, or Firm*—Richard O. Gray, Jr.

[57] ABSTRACT

An intravenous lead for use with a cardiac device for implantation in the coronary sinus or the coronary sinus and great cardiac vein of the heart provides positive fixation for the lead when implanted in the coronary sinus or the coronary sinus and great vein of the heart. The lead includes a lead body adapted to be fed into the coronary sinus and great vein of the heart of a patient and at least one electrode carried by the lead body and adapted to be coupled to the implantable cardiac device. The lead body includes a preformed section having a resiliently coiled configuration. The coiled section is a left-handed turned coiled section which provides superior positive fixation of the lead as compared to right-handed turned coiled sections for use in the coronary sinus and great cardiac vein.

16 Claims, 2 Drawing Sheets

CORONARY SINUS CHANNEL LEAD AND METHOD

BACKGROUND OF THE INVENTION

The present invention generally relates to an intravenous cardiac lead and method having an improved configuration for fixing the lead in a desired position within a vein or an artery after implantation. The present invention is more particularly directed to such an intravenous lead for use with an implantable atrial defibrillator which provides cardioverting electrical energy to the atria of the heart when the heart is in need of cardioversion. The intravenous cardiac lead of the present invention is particularly adapted for implantation in the coronary sinus or the coronary sinus and the great cardiac vein of the heart and includes at least one electrode adapted to be within the coronary sinus or great vein of the heart and a second electrode adapted to be within the right atrium of the heart when the lead is fed into the heart to a preferred position to enable the sensing of atrial activity of the heart and the delivery of the cardioverting electrical energy to the atria.

Atrial fibrillation is probably the most common cardiac arrhythmia. Although it is not usually a life threatening arrhythmia, it is associated with strokes thought to be caused by blood clots forming in areas of stagnant blood flow as a result of prolonged atrial fibrillation. In addition, patients afflicted with atrial fibrillation generally experience palpitations of the heart and may even experience dizziness or even loss of consciousness.

Atrial fibrillation occurs suddenly and many times can only be corrected by a discharge of electrical energy to the heart through the skin of the patient by way of an external defibrillator of the type well known in the art. This treatment is commonly referred to as synchronized cardioversion and, as its name implies, involves applying electrical defibrillating energy to the heart in synchronism with a detected ventricular electrical activation (R wave) of the heart. The treatment is very painful and, unfortunately, most often only results in temporary relief for patients, lasting but a few weeks.

Drugs are available for reducing the incidence of atrial fibrillation. However, these drugs have many side effects and many patients are resistant to them which greatly reduces their therapeutic effect.

Implantable atrial defibrillators have been proposed to provide patients suffering from occurrences of atrial fibrillation with relief. Unfortunately, to the detriment of such patients, none of these atrial defibrillators have become a commercial reality.

Two such proposed defibrillators, although represented as being implantable, were not fully automatic, requiring human interaction for cardioverting or defibrillating the heart. Both of these proposed defibrillators require the patient to recognize the symptoms of atrial fibrillation with one defibrillator requiring a visit to a physician to activate the defibrillator and the other defibrillator requiring the patient to activate the defibrillator with an external magnet.

An improved implantable atrial defibrillator and lead system which exhibits automatic operation is fully described in U.S. Pat. No. 5,282,837, issued Feb. 1, 1994, in the names of John M. Adams and Clifton A. Alferness for ATRIAL DEFIBRILLATOR AND METHOD, which patent is assigned to the assignee of the present invention and is incorporated herein by reference. The atrial defibrillator disclosed in the aforementioned referenced patent is truly automatic by including an atrial fibrillation detector which, responsive to sensed atrial activity, determines when the atria of the heart are in need of cardioversion. When the atrial fibrillation detector determines that the atria are in fibrillation and thus in need of cardioversion, the atrial fibrillation detector causes a cardioverter stage to deliver defibrillating or cardioverting electrical energy to the atria in timed relation to a detected ventricular electrical activation (R wave) of the heart. As a result, the atria are automatically and safely cardioverted.

As also disclosed in the aforementioned cross-referenced application, the quantity of electrical energy which is required to cardiovert or defibrillate the atria is reduced by an intravenous lead having an electrode adapted to be within the right atrium and another electrode adapted to be within the coronary sinus or the great cardiac vein beneath the left atrium. The application of the cardioverting electrical energy across these electrodes not only reduces the energy required to cardiovert the atria, but also reduces the amount of energy applied to the ventricles. To place the electrodes in the positions noted above, the lead is fed down the superior vena cava, into the right atrium, through the coronary sinus ostium, and advanced into the coronary sinus and the great cardiac vein. The lead is also preformed to generally conform to the shape of the coronary sinus and great vein to assist in holding the lead in place after implantation.

While the above-mentioned lead is preshaped to conform to the lead feed path to assist in holding the lead in place after implantation, it is desirable to provide the lead with more positive fixation since the blood flow through the coronary sinus is in a direction which tends to force the lead in a direction reverse to the feed path and out of the coronary sinus. Such positive fixation, however, must permit adequate blood flow through the coronary sinus and not cause occlusions.

U.S. application Ser. No. 08/147,330, filed Nov. 3, 1993, in the names of Clifton A. Alferness and John R. Helland, for INTRAVENOUS CARDIAC LEAD WITH IMPROVED FIXATION AND METHOD, now U.S. Pat. No. 5,387,233, assigned to the assignee of the present invention and incorporated herein by reference, describes an intravenous lead and method of implanting the same which provides such positive fixation. Fixation of the lead is provided by a preformed section of the lead which has a resiliently coiled configuration. After the lead is implanted within a vein or an artery, such as the coronary sinus or the coronary sinus and great cardiac vein, the preformed section is permitted to assume its coiled configuration for making substantially continuous surface contact with inner wall surfaces of the coronary sinus or great vein in the region of the coiled section. Such surface contact fixes the lead in place. Thereafter, fibrous tissue which builds up around the lead assures permanent fixation.

While the lead and method of the copending application mentioned above provides an elegant solution for fixing an intravenous lead within an artery or vein, such as the coronary sinus or the coronary sinus and great cardiac vein, a further refinement has been realized. This further refinement provides additional assurance that the lead will remain in a fixed position after implantation.

As is well known in the art, electrode or lead migration after implantation can have serious consequences in both being able to sense heart activity and effectively provide therapy to the patient. Loss of electrogram signals needed for diagnosis can occur and energy thresholds for providing needed therapy can become excessively high. Hence, any improvement towards electrode and lead fixation is important.

SUMMARY OF THE INVENTION

The present invention therefore provides an intravenous lead for use with a cardiac device and for implantation and fixation within the coronary sinus or the coronary sinus and great vein of a human heart. The lead includes a lead body adapted to be fed into the coronary sinus and great vein of the heart, at least one electrode carried by the lead body and adapted to be coupled to the cardiac device, wherein the lead body includes a left-handed turned coiled section.

The present invention further provides an intravenous lead for use with a cardiac device and for implantation and fixation within the coronary sinus or the coronary sinus and great vein of a human heart. The lead includes an inner styler coil, an outer electrically insulative jacket coaxial with and overlying said inner stylet coil, and an elongated electrode overlying said electrically insulative jacket. The inner styler coil includes a left-handed turned coiled portion for imparting a left-handed turned coiled configuration to the lead.

The present invention further provides a method of implanting an intravenous cardiac lead within the coronary sinus or the coronary sinus and great vein of the human heart. The method includes the steps of providing a cardiac lead having a flexible lead body, feeding the lead body to a predetermined position within the coronary sinus or great vein of the heart, and imparting a left-handed turned coiled configuration to the lead body for making substantially continuous surface contact with inner wall surfaces of the coronary sinus or great vein.

The present invention still further provides an intravenous lead for use with a cardiac device and for implantation and fixation within an artery or vein of the heart, wherein the artery or vein has a direction of curvature. The lead includes a lead body adapted to be fed into the artery or vein of the heart, and at least one electrode carried by the lead body and adapted to be coupled to the implantable cardiac device. The lead body includes a coiled section wherein the coiled section is turned in a direction opposite the direction of curvature of the artery or vein.

The present invention still further provides a method of implanting an intravenous cardiac lead within an artery or a vein of the human heart, wherein the artery or vein has a direction of curvature. The method includes the steps of providing a cardiac lead having a flexible lead body, feeding the lead body to a predetermined position within the artery or vein of the heart, and imparting a coiled configuration to the lead body for making substantially continuous surface contact with inner wall surfaces of the artery or vein, the coiled configuration being turned in a direction opposite the direction of curvature of the artery or vein.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawings, in the several figures of which like reference numerals identify identical elements, and wherein:

DETAILED DESCRIPTION OF THE PREFERRED EMBODIMENTS

Figure 1:
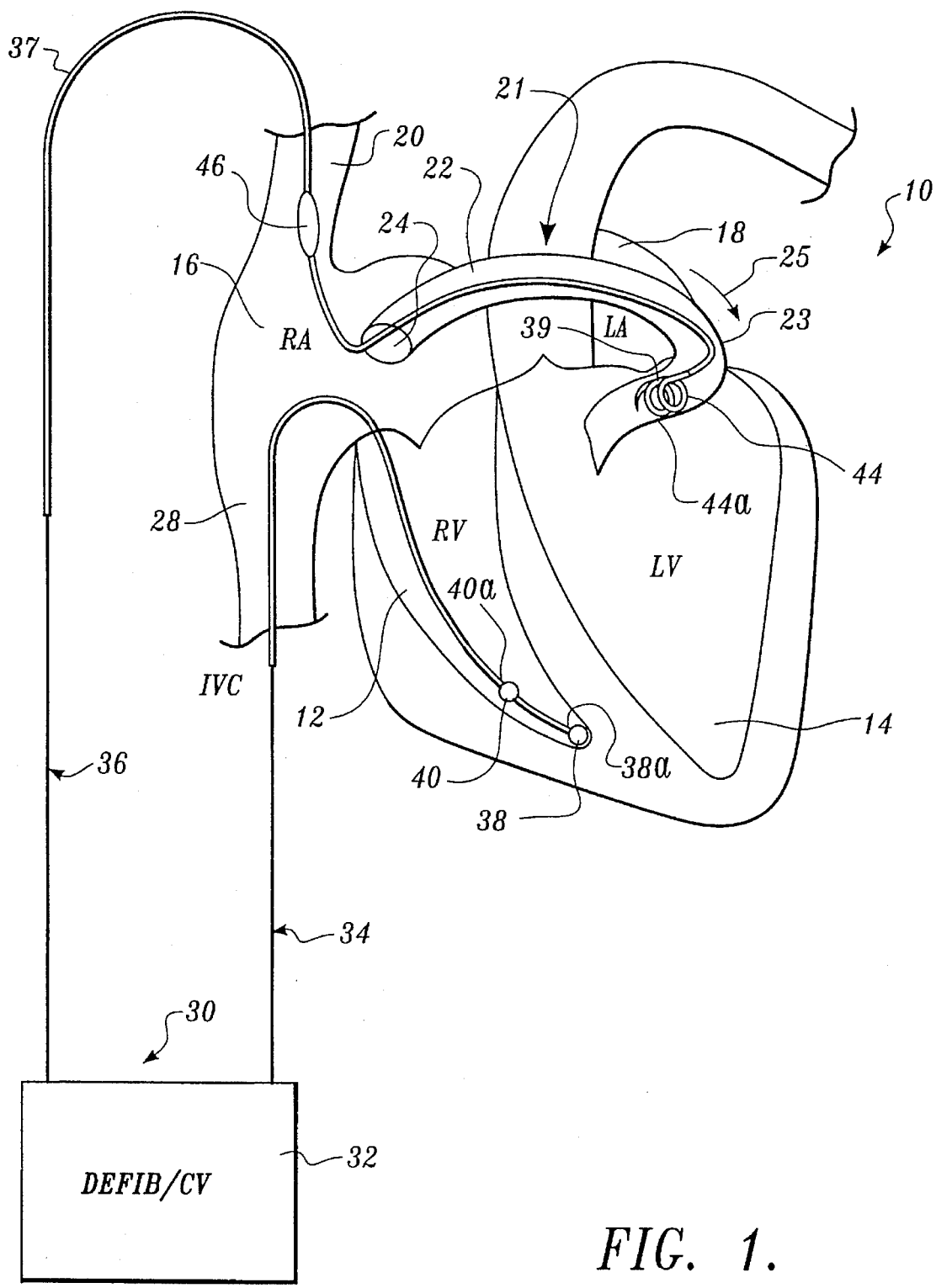
FIG. 1 is a schematically illustrated fully implantable atrial defibrillator shown in use with an intravenous lead embodying the present invention and in association with a human heart in need of atrial fibrillation monitoring and potential cardioversion.

Referring now to FIG. 1, it illustrates a fully implantable atrial defibrillator 30 shown in association with a schematically illustrated human heart 10 in need of atrial fibrillation monitoring and potential cardioversion of the atria. The portions of the heart 10 illustrated in FIG. 1 are the right ventricle 12, the left ventricle 14, the right atrium 16, the left atrium 18, the superior vena cava 20, the coronary sinus channel 21 which, as used herein, denotes the coronary sinus 22 and the great cardiac vein 23, the coronary sinus ostium or opening 24, and the inferior vena cava 28. In addition, as used herein, the term "ventricular electrical activations" denotes R waves of the heart cardiac cycle which induce depolarizations of the ventricles 12 and 14.

The atrial defibrillator 30 includes circuitry (not shown) which is contained within an enclosure 32. The enclosure 32 hermetically seals the internal circuit elements of the atrial defibrillator. The atrial defibrillator is shown in use with an endocardial first lead 34, and an intravenous second lead 36 embodying the present invention. The enclosure 32 and first and second leads 34 and 36 are arranged to be implanted beneath the skin of a patient so as to render the atrial defibrillator 30 fully implantable.

The endocardial first lead 34 preferably comprises an endocardial bi-polar lead having electrodes 38 and 40 arranged for establishing electrical contact with the right ventricle 12 of the heart 10. The electrodes 38 and 40 permit bi-polar sensing of ventricular electrical activations (R waves) in the right ventricle between a first pair of locations 38a and 40a within the right ventricle 12. As illustrated, the lead 34 is fed through the inferior vena cava 28, into the right atrium 16, and then into the right ventricle 12. As will be appreciated by those skilled in the art, a second path for lead 34 could alternatively be through the superior vena cava 20, into the right atrium 16, and then into the right ventricle 12.

The second or intravenous lead 36 embodying the present invention generally includes a lead body 37 which carries an elongated distal electrode 44 and an elongated proximal electrode 46. As illustrated, the lead body 37 is flexible and includes a preformed section 39 which includes electrode 44 and which has a resiliently coiled configuration. Because the lead body 37 is flexible, the preformed section 39 including electrode 44 may be elongated during implantation to reduce its effective cross-sectional diameter dimension to permit the lead 36 to be passed down the superior vena cava 20, into the right atrium 16, into the coronary sinus ostium 24, and advanced into the coronary channel 21 of the heart near the left side to a predetermined position where the electrode 44 is within either the coronary sinus 22 or the great cardiac vein 23 beneath the left atrium 18 near the left ventricle 14. The electrodes are preferably spaced apart relative to one another on lead body 37 so that when electrode 44 is positioned as described above, electrode 46 is within the right atrium 16 after the preformed resilient coiled section 39 is permitted to assume its coiled configuration through the release of the elongation of section 39. As a result, upon such release, the section 39 makes substantially continuous surface contact with the inner wall surfaces of the coronary sinus 22 or the great vein, as illustrated. This surface contact serves to provide positive fixation of lead 36 in the position illustrated. The contact between the coiled section 39 and the inner wall surface of the coronary sinus 22 or great vein 23 promotes the growth of fibrous tissue around the lead in the region of section 39 for permanent fixation of the lead 36.

The distal electrode 44 of lead 36 and the electrode 38 of the first lead 34 permit bi-polar sensing of ventricular electrical activations (R waves) between a second pair of locations 38a and 44a of the heart. As will be noted in FIG. 1, the spacing between the second pair of locations 38a and 44a is greater than the spacing between the first pair of locations 38a and 40a. As fully disclosed in copending application Ser. No. 07/861,184, filed on Mar. 31, 1992, in the names of John M. Adams, Clifton A. Alferness and K. Ross Infinger, for IMPROVED APPARATUS AND METHOD FOR RELIABLY DETECTING A DEPOLARIZATION ACTIVATION WAVE OF THE HEART AND ATRIAL DEFIBRILLATOR UTILIZING SAME, which application is assigned to the assignee of the present invention, these relative spacings between the first and second pairs of locations between which ventricular electrical activations are sensed enable reliable detection of R waves.

The electrode 44, together with the proximal electrode 46 of lead 36, provide for the delivery of defibrillating or cardioverting electrical energy to the atria. Because the ring electrode 44 is located beneath the left atrium 18 near the left ventricle 14 and the proximal electrode 46 is within the right atrium 16, the electrical energy applied between these electrodes will be substantially confined to the atria 16 and 18 of the heart 10. As a result, the electrical energy applied to the right ventricle 12 and left ventricle 14 will be minimized when the atria are cardioverted or defibrillated.

To determine when cardioversion or defibrillation of the atria of the heart 10 is required, the electrodes 44 and 46 also provide bi-polar sensing of electrical activity in the atria 16 and 18 of the heart 10. A microprocessor (not shown), as described in the aforementioned U.S. Pat. No. 5,282,837, digitizes the electrical signal provided by the electrodes 44 and 46 and processes the digitized values of the atrial activity for detecting atrial fibrillation. Such atrial fibrillation detection may be implemented as described in the aforementioned U.S. patent.

As will be appreciated by those skilled in the art, the lead 36 may be implanted as illustrated using the prior art technique of sliding a guide wire or styler into a central passageway of the lead. The guide wire may be preshaped to assist in guiding the lead 36 along the path previously described. The styler not only serves to guide or steer the lead 36 along the desired path, but in addition, serves to elongate coiled section 39 to reduce its effective cross-sectional diameter dimension to permit the lead to be fed into the heart. Once the lead reaches a predetermined position within the heart, such as, for example, corresponding to the electrode 44 being located either within the coronary sinus 22 or the great cardiac vein 23, the guide wire is retracted from the lead.

The retraction of the guide wire from the lead 36 releases the elongation of the coiled section 39 permitting the coil section to resiliently assume its coiled configuration as illustrated. Upon assuming its coiled configuration, the coiled section 39 will have a cross-sectional outer diameter dimension corresponding to the inner diameter dimension of the artery or vein in which it resides and in accordance with this preferred embodiment, the inner diameter dimension of the coronary sinus 22 or great cardiac vein 23.

As a result of the foregoing, the coiled section 39 will make substantially continuous surface contact with the inner surface of the coronary sinus 22 or great vein 23. This contact, together with the force exerted by the coiled section 39 against the inner wall surfaces of the coronary sinus 22 or great vein 23, provides positive fixation of lead 36. Also, as a result of the surface contact between coiled section 39 and the inner surface of the coronary sinus 22 or great vein 23, fibrous tissue will grow around the lead body 37 in the region of the coiled section 39 to provide permanent fixation of lead 36.

Even though the coiled section 39 provides positive fixation of lead 36, it will not adversely effect blood flow through the coronary sinus 22. Blood within the coronary sinus 22 will freely flow through the inner diameter dimension of the coiled section 39. Also, because of such free flow, the formation of occlusions through blood clotting will not occur.

As will be further noted in FIG. 1, and in accordance with one aspect of the present invention, the coiled section 39 is a left-handed turned coiled section. The left-handed turned coiled section for use in the coronary sinus 22 or great vein 23 has unexpectedly been found to have superior fixation qualities as compared to a right-handed turned coiled section for the same purpose. This result has actually been observed in practice in sheep hearts, which have structural characteristics very similar to the hearts of humans in terms of size and physiology. Over a dozen leads, each having a right-handed turned coiled section, have been implanted and nearly one-third of these leads became dislodged and suffered migration. In contrast, over a dozen leads, each having a left-handed coiled section, have been implanted with none of these leads becoming dislodged, and thus did not evidence migration. Both types of leads were identical except for the direction in which the coiled sections were turned. With the leads having the left-handed turned coiled sections, detected electrogram signals remained of constant quality, and energy thresholds for cardioverting the atria remained essentially constant.

To explain why this unexpected result occurred, it is postulated that superior fixation is achieved when the coiled section is turned in a direction which is opposite the direction of curvature of the artery or vein, as seen by the lead as it is fed to its desired position. It is believed that the opposite turn direction of the coiled section results in a greater resistance to dislodgement as compared to a turn direction which is the same as the direction of curvature of the artery or vein.

In the embodiment of FIG. 1, it can be seen that the coronary sinus 22 and great cardiac vein 23 have a direction of curvature 25 which is to the right, as would be down the lead 36 from a proximal point such as where the lead enters the coronary sinus ostium 24 to the distal end of the lead which includes electrode 44. The leads having superior fixation characteristics were those leads having a left-handed turned coiled section, as illustrated in FIG. 1. Hence, the coiled sections of those leads were turned in a direction opposite the direction of curvature of the artery or vein (coronary sinus, great cardiac vein) in which they were implanted, wherein "direction of curvature of the artery or vein" is meant to define the lateral displacement of the lead as seen distally down the lead from a point proximal to the distal end once the lead has reached a desired position within the artery or vein. It will also be noted that the coiled section 44a lies within the portion of the artery or vein which results in the above-noted direction of curvature.

Figure 2:
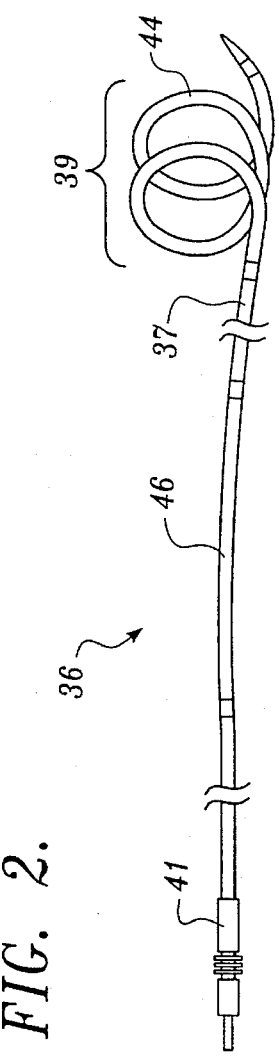
FIG. 2 is a perspective exploded view of an intravenous lead embodying the present invention; and, FIG. 3 is a partial, cross-sectional view, of the lead of FIGS. 2 and 3.

Referring now to FIG. 2, it shows the lead 36 embodying the present invention in an exploded partial perspective view. In addition to the structural elements of lead 36 previously described, the lead 36 further includes a connector 41 at its proximal end for coupling the electrodes 44 and 46 to an implantable cardiac device such as atrial defibrillator 30 of FIG. 1. As is well known in the art, an additional connector may be included so that each electrode is associated with its own respective connector.

Preferably, the coiled section is formed to have a free form cross-sectional outer diameter of, for example, eight (8) to twelve (12) millimeters. Also, although the coiled section 39 illustrated in FIG. 2 includes two loops, the coiled section 39 may have any number of loops as appropriate for a given application.

Figure 3:
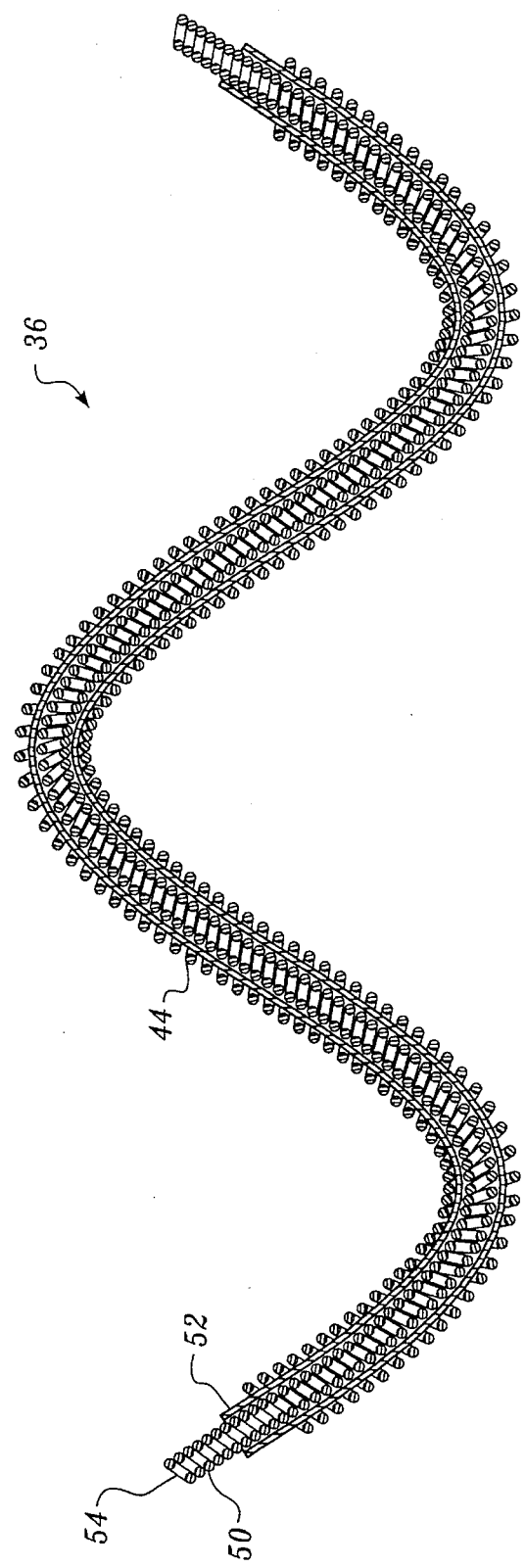

FIG. 3 is a partial cross-sectional view of the lead 36 within the section 39. More specifically, FIG. 3 shows in cross section one coil turn of the coiled configuration of the The lead 36, as lead 36 within the coiled section 39. illustrated in FIG. 3, includes an inner stylet coil 50, an outer electrically insulative jacket 52, and the elongated electrode 44.

The styler coil 50 is formed by a plurality of closely spaced small diameter turns of wire. The stylet coil 50 thus includes a central passageway 54 into which a stylet may be extended prior to and during the implantation of the lead 36.

The outer jacket 52 is formed of an electrically insulative material such as polyurethane or silicone rubber. As will be noted in the figure, the insulative jacket 52 is coaxial with and overlies the inner styler coil 50.

The electrode 44, like the stylet coil 50, is also formed from a plurality of closely spaced turns of a conductive wire. The electrode 44 is preferably preformed with its closely spaced turns prior to being mounted upon the lead 36.

To impart the coiled configuration to the lead 36 within the section 39 as illustrated in FIGS. 1 and 2, either one or both of the elongated electrode 44 and the inner stylet coil 50 is coiled with a left-handed turn in a portion thereof corresponding to the section 39 having the coiled configuration. To that end, the stylet coil 50 may be coiled to form a left-handed turned helix having comparatively widely spaced turns before the insulative jacket 52 is slid over the stylet coil 50. Similarly, the electrode 44 may be coiled to form a left-handed turned helix having comparatively widely spaced turns prior to the electrode 44 being slid over the insulative jacket 50. With either construction, the lead 36 within the section 39 will be imparted with a coiled configuration for making substantially continuous surface contact with the inner wall surfaces of the coronary sinus or the great vein for retaining the lead 36 after it is implanted.

While particular embodiments of the present invention have been shown and described, modifications may be made. It is therefore intended to cover in the appended claims all such changes and modifications which fall within the true spirit and scope of the invention.

What is claimed is:

1. An intravenous lead for use with a cardiac device and for implantation and fixation within the coronary sinus or the coronary sinus and great vein of a human heart, said lead comprising:

a lead body adapted to be fed into the coronary sinus and great vein of the heart; and at least one electrode carried by said lead body and adapted to be coupled to said cardiac device, said lead body including a left-handed turned coiled section.

2. An intravenous lead for use with a cardiac device and for implantation and fixation within the coronary sinus or the coronary sinus and great vein of a human heart, said lead comprising:

an inner stylet coil;
an outer electrically insulative jacket coaxial with and overlying said inner stylet coil; and
an elongated electrode overlying said electrically insulative jacket,
said inner styler coil including a left-handed turned coiled portion for imparting a left-handed turned coiled configuration to said lead.

3. A lead as defined in claim 2 wherein said elongated electrode overlies said coiled portion.

4. A lead as defined in claim 2 wherein said lead has a distal end, and wherein said elongated electrode and said coiled portion are located at said distal end of said lead.

5. A method of implanting an intravenous cardiac lead within the coronary sinus or the coronary sinus and great vein of the human heart, said method comprising the steps of:

providing a cardiac lead having a flexible lead body;
feeding said lead body to a predetermined position within the coronary sinus or great vein of the heart; and
imparting a left-handed turned coiled configuration to said lead body for making substantially continuous surface contact with inner wall surfaces of the coronary sinus or great vein.

6. A method as defined in claim 5 wherein said providing step includes preforming a section of said lead body into a resiliently coiled left-handed turned configuration to form a preformed left-handed turned coiled section, wherein said feeding step includes feeding said lead body with said preformed left-handed turned coiled section elongated so as to be feedable into the coronary sinus or coronary sinus and great vein of the heart, and wherein said imparting step includes releasing the elongation of said preformed left-handed turned coiled section after the lead is fed to said predetermined position within the coronary sinus or coronary sinus and great vein of the heart to permit said preformed left-handed turned coiled section to assume said left-handed turned coiled configuration.

7. A method as defined in claim 6 wherein said providing step includes providing an electrode on said lead body overlying said preformed left-handed turned coiled section.

8. A method as defined in claim 5 wherein said lead body includes an inner styler coil, wherein said providing step includes preforming a section of said stylet coil into a left-handed turned coiled configuration to impart to said lead body a preformed resilient left-handed turned coiled section, wherein said feeding step includes feeding said lead body with said preformed resilient left-handed turned coiled section elongated so as to be feedable into the coronary sinus or the coronary sinus and great vein of the heart, and wherein said imparting step includes releasing the elongation of said preformed resilient left-handed turned coiled section after the lead is fed to said predetermined position of the heart to permit said preformed resilient left-handed turned coiled section to assume said left-handed turned coiled configuration.

9. A method as defined in claim 8 wherein said providing step includes providing an elongated electrode on said lead body overlying said preformed left-handed turned coiled section.

10. A method as defined in claim 9 wherein said lead has a distal end and wherein said providing step includes providing said elongated electrode on said lead body distal end.

11. A method as defined in claim 10 wherein said predetermined position corresponds to said elongated electrode being within the coronary sinus or great vein of the heart.

12. A method as defined in claim 5 wherein said providing step includes providing an elongated electrode on said lead body and preforming a section of said elongated electrode into a left-handed turned coiled configuration to impart to said lead body a preformed resilient left-handed turned coiled section, wherein said feeding step includes feeding said lead body with said preformed resilient left-handed turned coiled section elongated so as to be feedable into the coronary sinus or coronary sinus and great vein of the heart, and wherein aid imparting step includes releasing the elongation of said preformed resilient left-handed turned coiled section after the lead is fed to said predetermined position of the heart to permit said preformed resilient left-handed turned coiled section to assume said coiled configuration.

13. A method as defined in claim 12 wherein said lead has a distal end and wherein said providing step includes providing said elongated electrode on said lead body distal end.

14. A method as defined in claim 13 wherein said predetermined position corresponds to said elongated electrode being within the coronary sinus or great vein of the heart.

15. An intravenous lead for use with a cardiac device and for implantation and fixation within an artery or vein of the heart wherein the artery or vein has a direction of curvature, said lead comprising:

a lead body adapted to be fed into the artery or vein of the heart; and at least one electrode carried by said lead body and adapted to be coupled to said implantable cardiac device, said lead body including a coiled section, the coiled section being turned in a direction opposite the direction of curvature of the artery or vein.

16. A method of implanting an intravenous cardiac lead within an artery or a vein of the human heart, wherein the artery or vein has a direction of curvature, said method comprising the steps of:

providing a cardiac lead having a flexible lead body;

feeding said lead body to a predetermined position within the artery or vein of the heart; and imparting a coiled configuration to said lead body for making substantially continuous surface contact with inner wall surfaces of the artery or vein, said coiled configuration being turned in a direction opposite the direction of curvature of the artery or vein.

* * * * *

UNITED STATES PATENT AND TRADEMARK OFFICE
CERTIFICATE OF CORRECTION

PATENT NO. : 5,476,498
DATED : December 19, 1995
INVENTOR(S) : Gregory M. Ayers

It is certified that error appears in the above-identified patent and that said Letters Patent is hereby corrected as shown below:

| Column | Line |  |
|--------|------|--|
| 2 | 36 | insert --Copending-- before "U.S." |
| 3 | 16 | "styler" should be --stylet-- |
| 3 | 19 | "styler" should be --stylet-- |
| 5 | 47 | "styler" should be --stylet-- |
| 5 | 50 | "styler" should be --stylet-- |
| 7 | 19 | after "the" (2nd occurr.) insert --lead 36 within-- the coiled section 39.-- |
| 7 | 20 | no new paragraph before --The-- |
| 7 | 20 | after "as" delete --lead 36 within the coiled section 39.-- |
| 7 | 24 | "styler" should be --stylet-- |
| 7 | 31 | "styler" should be --stylet-- |
| 8 | 12 | "styler" should be --stylet-- |
| 8 | 49 | "styler" should be --stylet-- |

Signed and Sealed this

Thirtieth Day of April, 1996

Attest:

BRUCE LEHMAN

*Attesting Officer*   *Commissioner of Patents and Trademarks*